(12) United States Patent
Paillard et al.

(10) Patent No.: US 6,699,506 B1
(45) Date of Patent: Mar. 2, 2004

(54) PHARMACEUTICAL COMPOSITION WITH EXTENDED RELEASE OF MILNACIPRAN

(75) Inventors: Bruno Paillard, Romagnat (FR); Eric Goutay, Lauzerville (FR); Jean-Louis Avan, Villefranche de Lauragus (FR); Joël Bougaret, Lanta (FR)

(73) Assignee: Pierre Fabre Medicament, Boulogne (FR)

( * ) Notice: Subject to any disclaimer, the term of this patent is extended or adjusted under 35 U.S.C. 154(b) by 0 days.

(21) Appl. No.: 09/254,014

(22) PCT Filed: Aug. 26, 1997

(86) PCT No.: PCT/FR97/01525

§ 371 (c)(1),
(2), (4) Date: Feb. 26, 1999

(87) PCT Pub. No.: WO98/08495

PCT Pub. Date: Mar. 5, 1998

(30) Foreign Application Priority Data

Aug. 28, 1996 (FR) ............................................. 96 10528

(51) Int. Cl.$^7$ ............................ A61K 9/14; A61K 9/16; A61K 9/50
(52) U.S. Cl. .................. 424/489; 424/400; 424/490; 424/491; 424/492; 424/493; 424/494; 424/495; 424/496; 424/497; 424/498
(58) Field of Search ................... 424/400, 489, 424/490, 491, 492, 493, 494, 495, 496, 497, 498

(56) References Cited

U.S. PATENT DOCUMENTS 4,478,836 A * 10/1984 Mouzin et al.
5,026,560 A * 6/1991 Makino et al.
5,160,742 A * 11/1992 Mazer et al.
5,578,316 A * 11/1996 Bhardwaj et al.
5,910,319 A * 6/1999 Anderson et al.

FOREIGN PATENT DOCUMENTS

| EP | 0092391 A | 10/1983 |
| EP | 0296560 A | 12/1988 |
| EP | 0468187 A | 1/1992 |
| EP | 0516520 A | 12/1992 |
| WO | 9320071 A | 10/1993 |

OTHER PUBLICATIONS

Remington's Pharmaceutical Sciences, p. 1623 (1990).*

* cited by examiner

Primary Examiner—Thurman K. Page
Assistant Examiner—Amy E Pulliam
(74) Attorney, Agent, or Firm—The Firm of Hueschen and Sage

(57) ABSTRACT

The invention concerns a pharmaceutical composition with prolonged release, for oral administration of a single daily dose of 60 to 140 mg of Milnacipran, having a multiparticulate form containing a plurality of microgranules each comprising an active microsphere containing a saccharose and/or starch nucleus of a size between 200 and 2000 μm and containing 150 to 1000 μm of Milnacipran and a binding agent, each microgranule being coated with a film having a base of at least one polymer insoluble in water but permeable to physiological liquids, of a thickness between 20 and 100 μm, the said pharmaceutical composition enabling an in vitro release corresponding to the following pattern: between 10 and 55% of the dose released in 2 hours, between 40 and 75% of the dose released in 4 hours, between 70 and 90% of the dose released in 8 hours, between 80 and 100% of the dose released in 12 hours.

37 Claims, 3 Drawing Sheets

PHARMACEUTICAL COMPOSITION WITH EXTENDED RELEASE OF MILNACIPRAN

Figure 1:
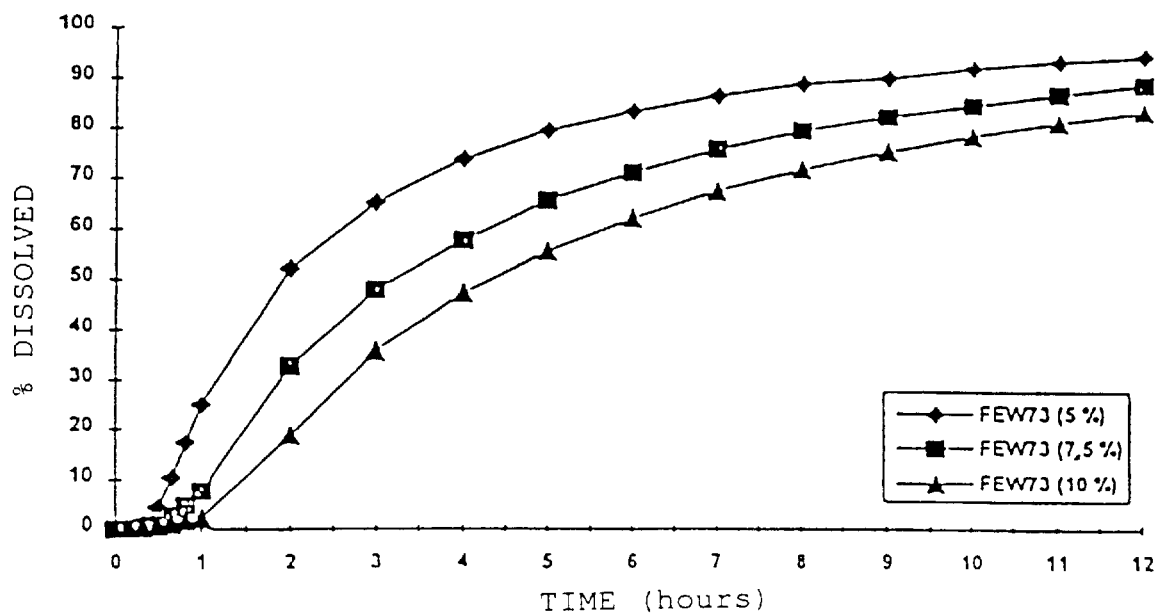

The present application is a U.S. National Application filed under 35 USC 371 of PCT/FR97/01525, filed Aug. 26, 1997 based upon French application Serial No. 96/10528 filed Aug. 28, 1996.

The subject of the present invention relates to the development of a multiparticulate form of the controlled-release minigranule type for the oral route, allowing the administration, in a single daily dose, of a particular antidepressant, namely: Milnacipran.

The novelty of this invention rests on the design of this minigranule or minisphere form which, by a combination:

of the Milnacipran concentration per minigranule,
of the physicochemical characteristics of the coating film,
and of the thickness of this film, makes it possible to control, surprisingly, the in-vitro release over several hours of a molecule whose aqueous solubility is close to 800 g/l, thereby making the single-dose administration of this entity possible.

Milnacipran and its Cis enantiomers exist in the form of hydrochlorides, whose aqueous solubilities are close to 800 g/l. Currently, these extremely soluble molecules, formulated with dicalcium phosphate, calcium carboxymethylcellulose and polyvinylpyrrolidone, packaged in gelatin capsules, do not allow this objective to be achieved since the in-vitro release from this 50 mg Milnacipran form is complete in thirty minutes thereby requiring the administration of a gelatin capsule in the morning and a gelatin capsule in the evening.

By contrast and surprisingly, the present invention relates to a prolonged-release galenic form, intended for oral administration in a single daily dose of 50 to 240 mg of Milnacipran, provided in a multiparticulate form combining a plurality of minigranules each containing an active minisphere comprising a sucrose and/or starch core having a particle size of between 200 and 2000 $\mu$m and containing 150 to 1000 $\mu$g of Milnacipran as well as a binding agent, each minigranule being coated with a film, based on at least one polymer insoluble in water but permeable to physiological fluids, having a thickness of between 20 and 100 $\mu$m, said galenic form allowing an in-vitro release corresponding to the following pattern:

between 10 and 55% of the dose released in 2 hours,
between 40 and 75% of the dose released in 4 hours,
between 70 and 90% of the dose released in 8 hours,
between 80 and 100% of the dose released in 12 hours.

This minigranule form containing a dose of 60 mg to 240 mg, more precisely 120 mg of Milnacipran in racemic form, or a therapeutically equivalent dose of Dextrorotatory Cis derivative, allows the therapeutic activity to be maintained over the nychthemeron while leveling the values of the plasma concentrations.

It will be recalled first of all that Milnacipran, a new antidepressant (patents Nos. FR 2,508,035-EP 200,638 and FR 2,640,972), exhibits a novel pharmacological activity since it allows a mixed inhibition of the capture of noradrenaline and serotonin, with no effect on dopamine.

Its chemical structure reveals two asymmetric carbons which confer on the molecule a Cis and Trans type isomerism, for which it has been demonstrated that the two Cis enantiomers are the active forms, preferably obtained by synthesis.

It has also been demonstrated that for these Cis derivatives the dextrorotatory form is more active than the levorotatory form.

Accordingly, the subject of the present invention applies both to the racemic molecule Milnacipran, but also to the two Cis enantiomers, since the physicochemical properties involved in the diffusional processes from the form remain identical.

Milnacipran and its Cis enantiomeric forms exhibit an absolute bioavailability greater than 85% and a biological half-life of between 7 and 9 hours, these properties being entirely compatible, from the pharmacokinetic point of view, with the design of a one-dose-per-day prolonged-release form.

In general, two distinct steps should be considered in the technical production of the prolonged-release minigranules, namely:

the active minisphere production phase,
the active minisphere film-coating phase.

Several technologies can be used for the production of the active minispheres:

mounting in a pan which consists of sprinkling the active ingredient with the aid of a binder on the sucrose or sucrose and starch cores also called nonpareils;

mounting in a fluidized air bed which consists in spraying a solution or a dispersion of active ingredient with the aid of a binder on the bed of nonpareils. This spraying may be performed from the top toward the bottom, from the bottom toward the top (Würster method) or tangentially (rotor method). In the latter case, the active ingredient may be sprayed in solid form concomitantly with the wetting liquid, with the aid of a feed hopper;

rotogranulation which makes it possible to obtain spherical grains from a suitable active agent-excipient mixture over which a binding solution is sprayed. This technology can be performed using rotogranulators combined or otherwise with a fluidized air bed;

extrusion-spheronization which allows the production of spherical grains. It involves obtaining, starting with a suitable active agent-excipient mixture, a plastic mass after mixing with a binding solution.

The plastic mass is then extruded using various systems which make it possible to convey and/or extrude this mass (barrel extruder, gear, piston, single- or twin-screw extruder, with axial or radial extrusion).

The extrudates obtained are then spheronized in a suitable spheronizer.

Conventionally, two techniques are used for the production of coated minigranules:

pan: the uncoated active minispheres are introduced into a perforated or nonperforated pan. A solution or dispersion of coating is then sprayed over the bed of minispheres with the aid of a gun or nozzle and any other suitable system allowing the production of a continuous, uniform and reproducible film;

fluidized air bed: depending on the spraying mode chosen, the film-coating of the active minispheres may be carried out by "top-spray", by "bottom-spray" or by "tangential-spray". The latter two techniques give a more uniform, more continuous and more reproducible coating than the first technique.

The major problem with which persons skilled in the art are confronted for the development of a prolonged-release form in general and of the minigranule type in particular, is the aqueous a solucility of the molecule.

In the present case, Milnacipran as well as its active enantiomers are very easily soluble in water (solubility=800 g/l). It should be recalled that it is impossible to use the base forms for reasons of stability.

Indeed, it is known to persons skilled in the art that with such molecules, the formulator who has to develop a prolonged-release form is confronted with the following antinomic problem:

avoiding the phenomenon of sudden discharge which is very frequent with this type of molecule and which, in some cases, is synonymous with side effects, and ensuring a perfect control of the release of the entire administered dose so as to avoid any loss of product.

Some formulators have solved this problem:

by combining within the same formulation several minigranule fractions (DE-3,941,703), an uncoated fraction providing the release during the first few minutes, and a fraction coated with a large amount of polymer controlling the diffusion during the subsequent hours, or by combining within the same formulation minigranules with multilayer film-coatings (U.S. Pat. No. 4,894, 240-WO-9 3097 67) or chemical compositions of coating polymers of a heterogeneous nature (EP-508 653-EP-0 322 277).

The present invention provides, through the design of this minigranule form for prolonged release of Milnacipran, having an aqueous solubility equal to 800 g/l, a solution which is less constraining for the developer.

Indeed, the formulas which are the subject of the present invention make it possible, through their design (content of active ingredient per minigranule, thickness of the film and composition of the film), to achieve an in-vitro release which is compatible with the therapeutic objective while using only one type of minigranules per formula.

It is very difficult, because of the absence of references, to describe, for a molecule with a solubility greater than 500 g/l, what would be the design for a minigranule form manufactured by the fluidized air and/or pan technology.

By way of comparison, reference may be made to the publication "Chlorpheniramine maleate controlled release spheres, I—Effect of ethyl cellulose and dibutyl sebacate levels", A. R. Oritz LABRADOR, E. S. CHALY (#1146), Proceed. Intern. Symp. Control. Rel. Bioact. Mater., 20, 1993 where the authors apply up to 30% Ethyl cellulose combined with Dibutyl sebacate in order to obtain a delayed release profile.

In patent EP-350 246, an organic base is used as release modulating agent.

In patent WO-953 491, inorganic bases are used as supports controlling the release.

In the document WO-9 201 446, hydrophobic substances (paraffin, waxes, stearyl alcohol) combined with a film of an acrylic nature are used to control the release of soluble active agents such as salbutamol, chlorpheniramine maleate.

It is obvious for persons skilled in the art that this type of formulation is very difficult to produce in and to transpose to a fluidized air bed.

In patent EP-249 949, the formulator produces a premix of soluble molecule with a nonionic polymer and an inorganic filler, before spraying them on the nonpareil, on which they then apply the insoluble film. In this example, there is in fact an intermediate layer limiting the diffusion of the active ingredient toward the coating film.

The solution proposed in the context of the present invention is much simpler and more easily industrializable, as shown more particularly in Examples Nos. 13, 14 and 15 below, because it provides a minigranule form composed of a single type of spheroids:

whose non-film-coated core has a size advantageously between 710 and 850 $\mu$m, whose active ingredient content per minigranule is preferably close to 510 $\mu$g, and whose film-coating based on ethyl cellulose in ethanolic solution is advantageously between 4% and 12.5%, that is to say a low thickness of 20 $\mu$m to 80 $\mu$m per minigranule.

Other characteristics and advantages of the present invention will be even understood on reading the detailed description given below, especially with regard to a number of specific exemplary embodiments.

The components which can be used for mounting Milnacipran in a pan are:

minispheres composed of sucrose and/or starch, also called nonpareils. These nonpareils were obtained by successive depositions of sucrose and/or starch on a sucrose crystal. The nonpareils used are preferably composed of 75% sucrose and 25% starch.

The nonpareils have various sizes ranging from 200 microns to 2 mm.

The nonpareils used preferably have a size of between 500 and 1000 microns and more particularly between 710 and 850 microns.

a binding agent sprayed in solution on a bed of minispheres. This binding agent may be a cellulose derivative such as hydroxypropylmethylcellulose, methyl cellulose, hydroxypropylcellulose, carboxymethylcellulose, may be gelatin, may be a solution of sucrose, may be a gum such as gum arabic, gum tragacanth, guar gum, pectins and alginates. It may be derived from polyvidone such as polyvinylpyrrolidone of different molecular weights.

The amount of these binders in the wetting solution may be up to 3 to 50%, and in the finished product from 0.5 to 30%.

The binder used is preferably polyvinylpyrrolidone having a molecular weight of close to 50,000 Da (type K30) in an amount of 20% in the wetting solution and in an amount of 2 to 4% in the active minispheres.

the solvent used to carry the binder may be an organic solvent of the type including methylene chloride, acetone, an alcohol such as isopropanol or ethanol, purified water or miscible combinations of these different solvent. The solvent used is preferably ethanol.

an agent intended to avoid the agglomeration of the minigranules to each other is advantageously used by sprinkling on the bed of cores.

Silica derivatives, metal oxides such as titanium oxide, silicates such as talc may be used in amounts of between 0.5 and 20% of the weight of the active minispheres. The talc is preferably used in an amount of between 3 and 4%.

Milnacipran is sprinkled on the bed of cores and its amount may be between 5 and 90% in the minispheres. This amount is preferably between 45 and 55% and is preferably 51%. That is to say a Milnacipran concentration per minigranule of between 450 $\mu$g and 550 $\mu$g and preferably of close to 510 $\mu$g since the active minisphere preferably weighs 1 mg.

The components used during the mounting of Milnacipran in a fluidized air bed are:

minispheres composed of sucrose and/or starch, also called nonpareils. These nonpareils were obtained by successive depositions of sucrose and/or starch on a sucrose crystal. The nonpareils used are preferably composed of 75% sucrose and 25% starch.

The nonpareils have various sizes ranging from 200 $\mu$m to 2 mm.

The nonpareils used preferably have a size of between 500 and 1000 $\mu$m and more particularly between 710 and 850 $\mu$m.

a binding agent sprayed in solution on the bed of minispheres. This binding agent may be a cellulose derivative such as hydroxypropylmethylcellulose, methyl cellulose, hydroxypropylcellulose, carboxymethylcellulose, may be gelatin, may be a solution of sucrose, may be a gum such as gum arabic, gum tragacanth, guar gum, pectins and alginates. It may be derived from polyvidone such as polyvinylpyrrolidone of different molecular weights.

The amount of these binders in the wetting solution may be up to 3 to 50%, and in the finished product from 0.5 to 30%.

The binder used is preferably polyvinylpyrrolidone having a molecular weight of close to 50,000 Da (type K30) in an amount of 0 to 20% and more precisely 6.7% in the wetting solution and from 5 to 25%, more precisely 15.4%, in the active minispheres.

The solvent used to carry the binder may be isopropanol and/or acetone, ethanol and/or acetone and is preferably isopropanol.

The Milnacipran is sprayed in the form of a dispersion in an amount of 10 to 40% in the solvent. Its preferred amount is 20% in the solvent.

The Milnacipran may represent 5 to 90% of the active minisphere. It is preferably between 40 and 50% and is preferably 46%.

That is to say a Milnacipran concentration per minigranule of between 150 and 185 $\mu$g and preferably of close to 170 $\mu$g when the nonpareils have a size of between 500 and 600 $\mu$m.

That is to say a Milnacipran concentration per minigranule of between 440 and 555 $\mu$g and preferably of close to 510 pig when the nonpareils have a size of between 710 and 850 $\mu$m.

That is to say a Milnacipran concentration per minigranule of between 680 and 850 $\mu$g and preferably of close to 780 $\mu$g when the nonpareils have a size of between 850 to 1000 $\mu$m.

The components used during the production of active minispheres during extrusion-spheronization are:

A diluent which may be of a hydrophilic or hydrophobic nature.

The component hydrophilic diluent may be of a cellulosic nature, such as microcrystalline cellulose, sodium cellulose or even hydroxypropylmethylcellulose. Lactose and starch may also be used.

The lipophilic diluent may be a monoglyceride, a diglyceride or a triglyceride.

These diluents represent 5 to 90% of the active minisphere. The diluent preferably used is microcrystalline cellulose in an amount of between 25 and 75% and preferably in an amount of 50%.

A binding agent. This binding agent may be a cellulose derivative such as hydroxypropylmethylcellulose, methyl cellulose, hydroxypropylcellulose, carboxymethylcellulose, may be gelatin, may be a, solution of sucrose, may be a gum such as gum arabic, gum tragacanth, guar gum, may be pectins or alginates. It may be derived from polyvidone such as polyvinylpyrrolidone of different molecular weights.

The amount of these binders in the wetting solution may be up to 0 to 50%.

This binding agent may vary from 0 to 20% in the active minispheres.

When the diluent is microcrystalline cellulose, it is not necessary to use a binding agent.

A solvent is used to wet the mixture of the different components and to make it an extrudable mass.

Alcohols such as ethanol or isopropanol may be used in combination or otherwise with purified water. Purified water is preferably used to wet the articles.

The active ingredient, during this operation, is introduced in an amount of between 5 and 90% of the weight of the active minispheres, preferably in an amount of between 25 and 75% of the weight of the active minispheres and more particularly of close to 50%. That is to say a Milnacipran concentration per minigranule preferably of between 250 and 750 $\mu$m and more particularly 500 $\mu$g.

The components used during the production of active minispheres during rotogranulation are:

A diluent which may be of a hydrophilic or hydrophobic nature.

The component hydrophilic diluent may be of a cellulosic nature, such as microcrystalline cellulose, sodium cellulose or even hydroxypropylmethylcellulose. Lactose and starch may also be used.

The lipophilic diluent may be a monoglyceride, a diglyceride or a triglyceride.

These diluents represent 5 to 90% of the active minisphere. The diluent preferably used is microcrystalline cellulose in an amount of between 40 and 60% and preferably in an amount of 50%.

A binding agent. This binding agent may be a cellulose derivative such as hydroxypropylmethylcellulose, methyl cellulose, hydroxypropylcellulose, carboxymethylcellulose, may be gelatin, may be a solution of sucrose, may be a gum such as gum arabic, gum tragacanth, guar gum, may be pectins or alginates. It may be derived from polyvidone such as polyvinylpyrrolidone of different molecular weights.

The amount of these binders in the wetting solution may be up to 0 to 50%.

This binding agent may vary from 0 to 20% in the active minispheres.

When the diluent is microcrystalline cellulose, it is not necessary to use a binding agent.

A solvent is used to wet the mixture of the different components and to make it an extrudable mass.

Alcohols such as ethanol or isopropanol may be used in combination or otherwise with purified water. Purified water is preferably used to wet the particles.

The active ingredient, during this operation, is introduced in an amount of between 5 and 90% of the weight of the active minispheres, preferably in an amount of between 40 and 60% of the weight of the active minispheres and more particularly of close to 50%. That is to say a Milnacipran concentration per minigranule preferably of between 500 and 750 $\mu$m and more particularly 625 $\mu$g.

The coating of the minispheres is composed of film-forming polymers insoluble in water but permeable to physiological fluids and which allow Milnacipran in solution to pass through by diffusion phenomena.

The coating agents traditionally used are derivatives of acrylic copolymers, alkyl celluloses, ethyl cellulose and lacquers of natural origin such as shellac gum.

Methacrylic copolymers of the poly(ethyl acrylate, methyl methacrylate) type in aqueous dispersion marketed under the name Eudragit NE30D, or of the poly(ethyl acrylate, methyl methacrylate, trimethylammoniumethyl methacrylate chloride) type in organic solvents (RS100 or RL100) or in aqueous dispersion RS30D/RL30D whose permeability depends on the amount of ammonium groups (RI>RS) are used in the invention.

The polymers are used in amounts of between 5 and 50% by weight of dry polymer relative to the weight of the active minispheres.

The polymer which is commercially called Eudragit RL100 or RL30D is not used in these amounts but respectively in combination with the polymers commercially called Eudragit RS100 or RS30D in amounts which may range from 1 to 20% of the overall amount of coating polymers.

Other coating agents such as ethyl cellulose of different grades are used. In the invention, the ethyl cellulose may be used in solution in a solvent such as dichloromethane, ethyl acetate, methanol and ethanol or a mixture of these solvents. Ethanol is preferably used.

The amount of ethyl cellulose represents, by weight of dry polymer, 2.5 to 50% of the weight of the active minispheres and is preferably between 3 and 15% and more particularly between 4 and 12.5%.

The ethyl cellulose may also be in the form of a ready-for-use aqueous dispersion such as Aquacoat ECD30 or Surelease which differs, inter alia, from Aquacoat ECD30 by the fact that the plasticizer is integrated into the dispersion.

The aqueous dispersions of ethyl cellulose are used in amounts of solid substances representing from 5 to 30% of the weight of the active minispheres. The amounts used preferably represent 12.5 to 17.5% of these minispheres.

It is possible to combine with these dispersions low-molecular weight hydroxypropylmethylcelluloses which are soluble in water, polyvinylpyrrolidone, low-molecular weight polyethylene glycols or any other soluble substances capable of promoting the creation of pores in the membrane in amounts of between 1 and 20% of the coating film. In our case, no soluble polymer was integrated into the formula.

The coating polymers used in this study were combined with plasticizers intended to improve the formation and the quality of the film.

The plasticizers used may be: dimethyl phthalate, diethyl phthalate, dibutyl phthalate, dibutyl sebacate, triethyl citrate, acetyltriethyl citrate, tributyl citrate, acetyltributyl citrate, triacetin, polyethylene glycols propylene glycol, glycerols, glycerides such as acetylated monoglyceride, fractionated coconut oil and castor oil.

The plasticizers are used in amounts of between 0 and 50% of the weight of dry polymer.

They are preferably used in amounts of between 15 and 25% of the weight of dry polymer.

The plasticizer used is preferably triethyl citrate in an amount representing 20% of the weight of dry polymer.

Filling agents are used, such as metal oxides, silicas, silicates, in particular magnesium silicate, in amounts of between 10 and 100% of the weight of dry polymer.

The amounts used with the acrylic derivatives are preferably between 50 and 100% of talc whereas they are between 20 and 70% with ethyl cellulose in ethanolic solution and preferably equal to 50%.

Antifoaming agents, such as silicone derivatives, may be integrated into the various formulations in amounts of between 0 and 0.5% of the active minispheres.

The invention will be understood more clearly with the aid of the following nonlimiting examples which constitute specific embodiments of the various processes which refer to various types of component according to the formula.

The examples going from 1 to 5 describe the processes and components used for the production of the active minigranules.

The examples going from 6 to 16 describe the processes and components used for the production of the coating for the active minigranules.

The technique for controlling in-vitro dissolution which is used to characterize these formulae is directly inspired by the USP XXIII monograph, DISSOLUTION, with the paddle apparatus (type 2), the speed of the paddles is set at 120 RPM, the dissolution medium is either phosphate buffer (0.066 M) pH=7.2, or purified water.

EXAMPLE NO. 1

Example 1 describes the production of minigranules containing Milnacipran doses using fixing of the active ingredient in a pan.

One kilogram of nonpareils having a size of between 710 and 850 microns is introduced into a laboratory-size solid pan. A 20% ethanolic solution of polyvinylpyrrolidone K30 is sprayed in order to wet the neutres and make them slightly sticky.

The Milnacipran, after sieving on a sieve with a mesh opening of 600 microns, is discharged with the aid of a shovel on the bed of cores. Talc may be introduced into the bed of core in the event of sticking. The cycle is terminated after a short drying which allows Milnacipran to completely adhere to the core.

The cycles are thus repeated in succession until the Milnacipran is finished.

After the fixing, a proportion of talc is deposited at the surface of the minigranule with the aid of the solution PVP K30 in order to isolate the Milnacipran from external moisture.

A final drying in a pan is carried out over a period of four hours which are in addition to the intermediate dryings carried out at the end of each cycle.

This fixing operation was carried out in a pilot- or semi-industrial-size pan. The procedure remains the same except that the quantities of raw materials are multiplied by a factor of 8 and 56.

| Components | Quantities used (kg) | | | Percentage formula (%) |
| --- | --- | --- | --- | --- |
| | Laboratory pan | Pilot pan | Semi-ind. pan | |
| Nonpareils | 0.832 | 6.658 | 46.60 | 42.62 |
| Milnacipran | 1.000 | 8.000 | 56.00 | 51.22 |
| PVP K30 | 0.048 | 0.382 | 2.70 ± (80%) | 2.45 |
| Talc | 0.072 | 0.580 | 4.06 | 3.71 |

During this mounting operation, the concentration per uncoated minigranule is close to 510 µg, leading for an administrable dose of 100 mg, to a composition containing about 195 minigranules.

EXAMPLE NO. 2

The process used in this example is that of the fluidized air bed equipped with a bottom-spraying system of the Wurster type. The apparatus used is of the GLATT trademark of the GPCG1 type.

A 6.7% concentrated Isopropanol solution of PVP K30 is prepared. The Milnacipran is added to this solution by dispersion with the aid of an Ultra-Turrax dispersing device for ten minutes. The Milnacipran represents 20.2% of the dispersion.

The dispersion is kept gently stirring during the process (propeller mixer). One kilogram of neutres, whose size may be between 500 and 600 µm, 710 and 850 µm or 850 and 1000 µm, is introduced into the Würster type feedstock tank.

The mean air inlet temperature is 65° C., the mean spraying rate is 20 g/min, the air flow rate 85 m$^3$/h, the spraying pressure 2 bar and the diameter of the spraying nozzle 1 mm.

Once the Milnacipran dispersion is finished, the minigranules are dried for 5 minutes in a fluidized air bed at 65° C. and then in a ventilated tank at 45° C. for 24 hours.

The procedure described above is transposed to a GPCG5-type pilot apparatus of the GLATT trademark.

The preparation of the Milnacipran dispersion in the isopropanolic solution of PVP K30 is carried out under the same conditions as above by multiplying the quantities used by a factor of 8.4.

8.4 kg of neutres, whose size is between 710 and 850 microns, are introduced into the Würster-type feedstock tank.

The mean air inlet temperature is 55° C., the mean spraying rate 150 g/min, the air flow rate 260 m³/h, the spraying pressure 3.5 bar and the diameter of the nozzle is 1.2 mm.

Once the Milnacipran dispersion is finished, the minigranules are dried for 5 minutes in a fluidized air bed at 55° C. and then in a ventilated oven at 45° C. for 24 hours.

Description of the formulae:

| Components | Quantities used (kg) | | Percentage formula (%) |
|---|---|---|---|
| | GPCG1 | GPCG5 | |
| Nonpareils | 1.00 | 8.40 | 38.46 |
| PVP K30 | 0.40 | 3.36 | 15.38 |
| Milnacipran | 1.20 | 10.08 | 46.15 |

During this mounting operation, the concentration per minigranule is close to 510 µg, leading, depending on the size of the gelatin capsule (sizes No. 1 to No. 00, to an administrable dose of 60 to 240 mg.

EXAMPLE NO. 3

The Milnacipran and an excipient, microcrystalline cellulose whose trade name is Avicel PH101, are mixed in equal parts (150 drams each) in a Turbula T2 type mixer for 10 minutes.

The mixture thus prepared is moistened in a Kenwood Major type planetary mixer.

The liquid used is purified water and its quantity is adjusted so as to obtain a plastic mass. The wetting time lasts for 5 minutes and the kneading 3 minutes.

The plastic mass thus obtained is extruded in a GABLER PHARMEX 35T type extruder with the aid of a screw 450 mm long for a diameter of 45 mm which rotates at a speed of 50 RPM.

The extrusion grid has 1 mm meshes and is oriented in the axis of he endless screw.

The extrusion is performed at room temperature.

The extrudates obtained are then spheronized with the aid of a GABLER SPHAEROMAT SPH 250 spheronizer whose speed is set at 1000 RPM for 1 minute and then at 120 RPM for 9 minutes.

The drying is carried out in a ventilated oven at a temperature of 40° C. until the residual moisture level is less than 3%.

The minigranules thus obtained have a particle size of between 1 mm and 1.4 mm and an elongation ratio of 0.86.
Description of the Formula:

| Components | Quantities used (g) | Percentage formula (%) |
|---|---|---|
| Milnacipran | 150 | 50 |
| Avicel PH101 | 150 | 50 |

During this mounting operation, the concentration per minigranule is close to 500 µg, leading, depending on the size of the gelatin capsule (sizes No. 1 to No. 00, to an administrable dose of 60 to 240 mg.

EXAMPLE NO. 4

The procedure used in this example is also extrusion-spheronization. However, the extrusion, unlike Example No. 3, is performed radially to the screw.

The mixing of the different components which vary in quality and in quantity as a function of the two formulas described is carried out in a LODIGE® granulator for 5 minutes at a constant speed.

The wetting liquid is purified water which represents, depending on the formulas, from 15 to 18% of the mass.

The plastic mass is radially extruded and forced at a constant speed through a grid 1 mm in diameter.

The extrudates obtained are spheronized in a batch of 500 g in a Colette Marumerizer spheronizer for 5 to 10 minutes depending on the formulas.

The minigranules obtained are dried for 24 hours at 40° C. in a ventilated oven.
Description of the Formulas:

| Components | FESR1 | | FESR2 | |
|---|---|---|---|---|
| | Quantities used (g) | Percentage formula (%) | Quantities used (g) | Percentage formula (%) |
| Avicel PH102 | 250 | 50 | 93.75 | 18.75 |
| Avicel CL611 | | | 31.25 | 6.25 |
| Milnacipran | 250 | 50 | 375.00 | 75.00 |

During this mounting operation, the concentration per minigranule is 400 µg or 1160 µg, leading, depending on the size of the gelatin capsule (sizes No. 1 to No. 00), to an administrable dose of 60 to 240 mg.

EXAMPLE NO. 5

In Example No. 5, the production of the minigranules containing Milnacipran doses is carried out by spherical granulation in a fluidized air bed.

The apparatus is characterized by a rotating disk whose distance from the wall of the feedstock tank makes it possible to modulate the admission of air. Under the combined action of rotation of the disk and the ascending air flow, the particles follow a spiral movement. At the same time, a wetting liquid is sprayed tangentially to the mixture. The combination of these operations leads to the production of spherical particles.

The mixing, composed of 250 g of Milnacipran and 250 g of Avicel PH101, is carried out in the feedstock tank for three minutes. The air is admitted at a flow rate of 100 m³/h and the rotating disk rotates at 180 RPM.

Inside the same apparatus, the wetting of the mass is performed by tangential spraying of purified water.

The spraying rate is at 20 g/min and the speed of rotation of the disk is increased from 180 RPM to 1080 RPM by an increase of 180 RPM every minute.

The air inlet temperature is 50° C., the spraying pressure is 2 bar and the diameter of the nozzle 1.2 mm.

During the wetting of the mixture, the particles agglomerate, giving grains which, by rolling on the smooth and cylindrical walls of the tank, become dense while taking on a spherical appearance.

Once the minigranules have been obtained, they are dried in the rotor tank for 10 minutes at 60 C and then for 12 hours at 40° C. in a ventilated oven.

These minigranules are characterized by a particle size distribution of between 7.00 and 1400 microns and an elongation factor of 0.85.

Description of the Formula:

| Components | Quantity used (g) | Percentage formula (%) |
|---|---|---|
| Avicel PH101 | 250 | 50 |
| Milnacipran | 250 | 50 |

During this mounting operation, the concentration per minigranule is close to 625 µg, leading, depending on the size of the gelatin capsule (sizes No. 1 to No. 00), to an administrable dose of 60 to 240 mg.

The examples going from 6 to 16 describe the processes and components used for carrying out the coating of the minigranules.

EXAMPLE NO. 6

Minigranules produced by the method described in Example No. 2 are coated with the aid of the same technological process.

180 g of film-forming polymer, whose trade name is Eudragit RS 100, are dissolved in 1500 g of an organic solution composed of 80% isopropanol and 20% acetone.

27 g of diethyl phthalate, which acts as plasticizer, are added to this solution.

90 g of talc acting as antiadhering agent are added to 750 g of an organic solution of the same comoosition as that described above. This proportion of talc is dispersed by an ultra-turrax-type polydispersing device.

This dispersion is incorporated into the Eiidragit RS100 solution and kept starring (propeller mixers) during the spraying. The coating preparation is kept stirring (propeller mixer) during the spraying.

The mean air inlet temperature is 45° C., the mean spraying rate is 10 g/min, the air flow rate 85 m³/h, the spraying pressure 1.5 bar and the diameter of the nozzle 0.8 mm.

Depending on the quantity of coating liquid deposited on the minigranules, the amount of dry coating polymer may represent 20%, 25% or 30% of the weight of the active minigranules.

Description of the formulas:

| | FEW49 | | | | | |
|---|---|---|---|---|---|---|
| | 20% | | 25% | | 30% | |
| Components | Quantities used (g) | Percentage formula (%) | Quantities used (g) | Percentage formula (%) | Quantities used (g) | Percentage formula (%) |
| Minigranules ex 2 | 500.00 | 75.20 | 500.00 | 70.80 | 500.00 | 66.90 |
| Eudragit RS100 | 100.00 | 15.05 | 125.00 | 17.70 | 150.00 | 20.10 |
| Diethyl phthalate | 15.00 | 7.50 | 18.75 | 2.65 | 22.50 | 3.00 |
| Microtalc | 50.00 | 2.25 | 62.50 | 8.85 | 75.00 | 10.00 |

The percentages dissolved are the following:

| | 0.50 h | 1 h | 2 h | 4 h | 8 h | 12 h | T 50% |
|---|---|---|---|---|---|---|---|
| 20% | 0.17 | 0.34 | 15.93 | 100.60 | 101.40 | 101.50 | 2 h 41 min |
| standard deviation | 0.47 | 0.42 | 3.65 | 1.26 | 1.20 | 1.12 | |
| 25% | 0.11 | 0.25 | 1.28 | 95.75 | 101.50 | 101.60 | 2 h 51 min |
| standard deviation | 0.02 | 0.06 | 0.46 | 0.17 | 0.07 | 0.016 | |
| 30% | 0.21 | 0.35 | 0.95 | 67.88 | 102.20 | 102.2 | 3 h 44 min |
| standard deviation | 0.03 | 0.06 | 0.36 | 1.87 | 0.20 | 0.43 | |

These formulas, whose Milnacipran concentration per uncoated minigranule is 510 µg and whose film thicknesses are equal to 112, 141 and 169 µm (surface masses equal to 4.74, 5.93 and 7.12 mg/cm²), do not make it possible to achieve the abovementioned objective in vitro.

EXAMPLE NO. 7

This example differs from the preceding one mainly in that the film-forming polymer used is provided in the form of an aqueous dispersion whose trade name is Eudragit RS30D, in that the plasticizer is triethyl citrate and in that the nonpareils have a size of between 850 and 1000 microns.

19 g of triethyl citrate are incorporated into 417 g of aqueous dispersion of Eudragit RS30D, with gentle stirring. 50 g of talc dispersed with the aid of an ultra-Turrax-type polydispersing device are introduced into 400 g of purified water. Once a homogeneous dispersion of talc is obtained, it is added to the first preparation and kept gently stirring during the entire duration of the spraying.

The air inlet temperature is between 50 and 55° C., the mean spraying rate is 10 g/min, the air flow rate is 85 m³/h, the spraying pressure 2 bar and the diameter of the nozzle 0.8 mm.

Depending on the quantity of coating liquid deposited on the minigranules, the amount of coating polymers may represent 20 or 25of the weight of the uncoated minigranules.

Description of the formulas:

FEW14

| | 20% | | 25% | |
|---|---|---|---|---|
| Components | Quantities used (g) | Percentage formula (%) | Quantities used (g) | Percentage formula (%) |
| Minigranules ex 2 | 500.00 | 76.30 | 500.00 | 72.00 |
| Eudragit RS30D | 100.00 | 15.30 | 125.00 | 18.00 |
| Triethyl citrate | 15.00 | 2.30 | 19.00 | 2.70 |
| Talc | 40.00 | 6.10 | 50.00 | 7.20 |

The percentages dissolved are the following:

| | 0.50 h | 1 h | 2 h | 4 h | 8 h | 12 h | T 50% |
|---|---|---|---|---|---|---|---|
| 20% | 0.34 | 2.05 | 66.02 | 94.05 | 99.59 | 100.29 | 1 h 44 min |
| standard deviation | 0.10 | 1.56 | 0.58 | 0.14 | 0.19 | 0.18 | |
| 25% | 0.33 | 0.60 | 10.67 | 89.37 | 100.63 | 101.90 | 2 h 36 min |
| standard deviation | 0.01 | 0.12 | 1.17 | 0.58 | 0.51 | 1.14 | |

These formulas, whose Milnacipran concentration per uncoated minigranule is 780 µg and whose film thicknesses are equal to 151 and 188 µm (surface masses equal to 5.5 and 6.85 mg/cm²), do not make it possible to achieve the abovementioned objective in vitro.

EXAMPLE NO. 8

This example differs from the preceding one in that the film-forming polymer used is Eudragit NE30D and no longer Eudragit RS30D, in that no plasticizer is used because the glass transition temperature of the polymer is low and in that 75% talc is used relative to the weight of the dry polymer and in that the nonpareils have a size of between 710 and 850 microns.

65.6 g of talc are dispersed with the aid of an ultra-turrax-type polydispersing device in 323.2 g of purified water. Once a homogeneous dispersion has been obtained, it is incorporated into 291.7 g of Eudragit NE30D with gentle stirring (propeller mixer). The dispersion thus obtained is kept stirring during the spraying.

The mean air inlet temperature is 35° C., the mean spraying rate is 10 g/min, the mean air flow rate 110 m³/h, the spraying pressure 2 bar and the diameter of the nozzle 0.8 mm.

Depending on the quantity of coating liquid deposited on the minigranules, the amount of dry coating polymer may represent 10, 12.5, 15, 17.5% of the weight of uncoated microgranules.

Description of the formulas:

FEW60

| | 10% | | 12.50% | | 15% | | 17.50% | |
|---|---|---|---|---|---|---|---|---|
| Components | Quantities used (g) | Percentage formula (%) | Quantities used (g) | Percentage formula (%) | Quantities used (g) | Percentage formula (%) | Quantities used (g) | Percentage formula (%) |
| Minigranules ex 2 | 500.00 | 85.10 | 500.00 | 82.50 | 500.00 | 79.20 | 500.00 | 76.55 |
| Eudragit NE30D | 50.00 | 8.50 | 62.500 | 10.25 | 75.00 | 11.90 | 87.50 | 13.40 |
| Microtalc | 37.50 | 6.40 | 46.875 | 7.70 | 56.25 | 7.9 | 65.625 | 10.05 |

The percentages dissolved are the following:

| | 0.50 h | 1 h | 2 h | 4 h | 8 h | 12 h | T 50% |
|---|---|---|---|---|---|---|---|
| 10% | 2.36 | 22.61 | 56.85 | 79.48 | 93.15 | 97.11 | 1 h 41 min |
| standard deviation | 0.95 | 0.79 | 0.41 | 0.54 | 0.63 | 0.61 | |
| 12.50% | 0.68 | 4.40 | 36.86 | 66.63 | 86.64 | 96.63 | 2 h 38 min |
| standard deviation | 0.18 | 0.65 | 1.29 | 0.51 | 0.16 | 0.22 | |
| 15% | 0.45 | 1.70 | 17.28 | 53.54 | 78.67 | 88.50 | 3 h 40 min |
| standard deviation | 0.19 | 0.44 | 1.00 | 0.07 | 0.16 | 0.04 | |
| 17.50% | 0.13 | 0.39 | 2.40 | 35.86 | 68.01 | 81.43 | 5 h 16 min |
| standard deviation | 0.20 | 0.26 | 0.60 | 0.72 | 0.74 | 0.72 | |

The formulas containing 10 and 17.5% polymer whose Milnacipran concentration per uncoated minigranule is 510 µg and whose film thicknesses are equal to 51 and 89 µm (surface masses equal to 2.15 and 3.94 mg/cm2) do not make it possible to achieve the abovementioned objective in vitro.

On the other hand, surprisingly, the formula containing 12.5% and 15% polymer, having a Milnacipran concentration per uncoated minigranule of 510 µg, whose film thickness is close to 63 and 76 µm (surface mass equal to 2.81 and 3.37 mg/cm$^2$) achieve the abovementioned objective in vitro.

These formulas containing unit doses of 60 to 240 mg, and more particularly of 100 mg and 150 mg of Milnacipran, can be placed in gelatin capsule of sizes No. 1 or No. 0+.

EXAMPLE NO. 9

Example No. 9 differs from the preceding examples mainly in that the coating polymer is no longer a copolymer of metha and ethacrylic acids acrylic but is ethyl cellulose provided in the form of an aqueous dispersion in an amount of between 24.5 and 29.5%. This dispersion is marketed under the name Aquacoat ECD30 and is also composed of a surfactant, sodium lauryl sulfate, in an amount of between 0.9 and 1.7% and a stabilizing agent, cethyl alcohol, in an amount of between 1.7 and 3.3%.

334 g of Aquacoat ECD are incorporated into 246 g of purified water, with gentle stirring (propeller mixer), and then 20 g of plasticizer, triethyl citrate, are added to the dispersion. To allow a good distribution of the plasticizer, the stirring is continued for 30 minutes before the beginning of the spraying during which it is maintained.

The mean air inlet temperature is 52.5° C., the mean spraying rate is 10 g/min, the air flow rate is 85 m$^3$/h, the spraying pressure is 2 bar and the diameter of the nozzle 0.8 mm.

Depending on the quantity of coating liquid deposited on the microgranules, the amount of dry coating polymer may represent 10, 15 or 20% of the weight of uncoated microgranules.

At the end of the spraying, drying in a fluidized air bed is performed at 40° C. for 5 minutes. The minigranules are then discharged and dried for 24 hours at 40° C. in a ventilated oven.

Depending on the quantity of coating liquid deposited on the microgranules, the amount of dry coating polymer may represent 10, 15 or 20% of the weight of uncoated minigranules.

| | Description of the formulas: | | | | | |
|---|---|---|---|---|---|---|
| | FEW16 | | | | | |
| | 10% | | 15% | | 20% | |
| Components | Quantities used (g) | Percentage formula (%) | Quantities used (g) | Percentage formula (%) | Quantities used (g) | Percentage formula (%) |
| Minigranules ex 2 | 500.00 | 89.30 | 500.00 | 84.70 | 500.00 | 80.60 |
| Aquacoat ECD30 | 50.00 | 8.90 | 75.00 | 12.70 | 100.00 | 16.10 |
| Triethyl citrate | 10.00 | 1.80 | 15.00 | 2.50 | 20.00 | 3.20 |

| | The percentages dissolved are the following: | | | | | | |
|---|---|---|---|---|---|---|---|
| | 0.50 h | 1 h | 2 h | 4 h | 8 h | 12 h | T 50% |
| 10% | 34.17 | 50.82 | 67.38 | 80.93 | 91.34 | 95.53 | 58 min |
| standard deviation | 2.73 | 3.05 | 2.90 | 2.20 | 1.48 | 1.08 | |
| 15% | 8.18 | 21.17 | 36.34 | 52.15 | 67.27 | 75.54 | 3 h 54 min |
| standard deviation | 0.76 | 0.78 | 0.54 | 0.43 | 0.36 | 0.35 | |
| 20% | 0.62 | 5.70 | 19.76 | 35.75 | 50.94 | 60.21 | 7 h 57 min |
| standard deviation | 0.18 | 0.66 | 0.53 | 0.92 | 0.92 | 0.49 | |

These formulas, whose Milnacipran concentration per minigranule is 510 µg and whose film thicknesses are equal to 75, 113 and 150 µm (surface masses equal to 2.74, 4.11 and 5.48 mg/cm$^2$), do not make it possible to achieve the abovementioned objective in vitro.

EXAMPLE NO. 10

This example differs from the preceding example in that the aqueous dispersion of ethyl cellulose is marketed under the name Surelease and in that its composition is different from Aquacoat ECD30.

This dispersion is composed of ethyl cellulose, a plasticizer which may be dibutyl sebacate or fractionated coconut oil also called miglyol, a coplasticizer stabilizing oleic acid and an aqueous ammonium hydroxide base. In this particular example, the plasticizer is dibutyl sebacate.

The preparation of the coating dispersion is carried out by incorporating 400 g of Surelease E-7-7050, with gentle stirring (propeller mixer), into 915 grams of purified water.

Depending on the quantity of coating liquid deposited on the microgranules, the amount of dry coating polymer may represent 10, 15 or 20% of the weight of the uncoated microgranules.

The coating operation as well as the drying of the minigranules are carried out in the same manner as in Example 10.

Description of the formulas:

| | FEW26 | | | | | |
|---|---|---|---|---|---|---|
| | 10% | | 15% | | 20% | |
| Components | Quantities used (g) | Percentage formula (%) | Quantities used (g) | Percentage formula (%) | Quantities used (g) | Percentage formula (%) |
| Minigranules ex 2 | 500.00 | 90.90 | 500.00 | 86.90 | 500.00 | 83.30 |
| Surelease E7-7050 | 50.00 | 9.10 | 75.00 | 13.10 | 100.00 | 16.70 |

The percentages dissolved the following:

| | 0.50 h | 1 h | 2 h | 4 h | 8 h | 12 h | T 50% |
|---|---|---|---|---|---|---|---|
| 10% | 32.48 | 50.61 | 68.51 | 84.90 | 97.32 | 101.32 | 1 h |
| standard deviation | 0.50 | 0.83 | 1.22 | 1.33 | 1.25 | 0.94 | |
| 15% | 7.15 | 18.48 | 35.99 | 56.38 | 75.96 | 86.65 | 3 h 14 min |
| standard deviation | 0.12 | 0.19 | 0.28 | 0.31 | 0.32 | 0.33 | |
| 20% | 0.77 | 2.66 | 11.27 | 32.54 | 51.83 | 62.68 | 7 h 28 min |
| standard deviation | 0.21 | 0.38 | 0.37 | 0.48 | 0.55 | 0.58 | |

The formulas containing 10 and 20% polymer whose Milnacipran concentration per uncoated minigranule is 510 µg and whose film thicknesses are equal to 52 and 103 µm (surface masses equal to 2.27 and 4.54 mg/cm$^2$) do not make it possible to achieve the abovementioned objective in vitro.

On the other hand, surprisingly, the formula containing 15% polymer, having a Milnacipran concentration per uncoated minigranule of 510 µg, whose film thickness is equal to 77.5 µm (surface mass equal to 3.41 mg/cm$^2$) achieves the abovementioned objective in vitro.

These formulas containing unit doses of 60 to 240 mg, and more particularly of 110 mg and 220 mg of Milnacipran, can be placed in gelatin capsule of sizes No. 1 or No. 00.

EXAMPLE NO. 11

This example differs from Examples Nos. 9 and 10 in that the coating polymer, ethyl cellulose, is no longer provided in the form of a dispersion but in the form of an ethanolic solution of the film-forming polymer.

50 g of ethyl cellulose are gradually incorporated in 900 grams of ethanol, with vigorous stirring (propeller mixer). The mixture is kept stirring for one hour.

25 grams of talc are dispersed in 300 g of ethanol with the aid of an Ultra-turrax type polydispersing device during the time required for the homogenization of the dispersion.

10 g of plasticizer, triethyl citrate, and the talc dispersion are added to the ethanolic solution of ethyl cellulose, with gentle stirring (propeller mixer). This stirring is maintained during the spraying.

During the coating operation, the mean air inlet temperature is 40° C., the mean spraying rate is 11 g/min, the mean air flow rate 85 m$^3$/h, the spraying pressure 2 bar and the diameter of the nozzle 0.8 mm.

The minigranules are then dried in a fluidized air bed at 35° C. for 5 minutes. An additional drying in a ventilated oven is carried out for 24 hours at 40° C.

Depending on the quantity of coating liquid deposited on the microgranules, the amount of dry coating polymer may represent 5, 7.5 or 10% of the weight of uncoated microgranules.

Description of the formulas:

| | FEW41 | | | | | |
|---|---|---|---|---|---|---|
| | 5% | | 7.50% | | 10% | |
| Components | Quantities used (g) | Percentage formula (%) | Quantities used (g) | Percentage formula (%) | Quantities used (g) | Percentage formula (%) |
| Microgranules ex 2 | 500.00 | 92.20 | 500.00 | 88.70 | 500.00 | 85.50 |
| Ethyl cellulose N22NF | 25.00 | 4.60 | 37.50 | 6.75 | 50.00 | 8.50 |
| Triethyl citrate | 5.00 | 0.90 | 7.50 | 1.30 | 10.00 | 1.70 |
| Talc | 12.50 | 2.30 | 18.75 | 3.30 | 25.00 | 4.30 |

-continued

| | The percentages dissolved are the following: | | | | | |
|---|---|---|---|---|---|---|
| | 0.50 h | 1 h | 2 h | 4 h | 8 h | 12 h | T 50% |
| 5% | 10.86 | 29.39 | 49.58 | 68.75 | 83.07 | 88.82 | 2 h |
| standard deviation | 0.36 | 0.25 | 0.33 | 0.22 | 0.08 | 0.18 | |
| 7.50% | 0.87 | 9.27 | 32.89 | 56.19 | 76.86 | 86.63 | 3 h 20 min |
| standard deviation | 0.02 | 0.54 | 0.40 | 0.80 | 1.34 | 1.55 | |
| 10% | 0.15 | 0.96 | 17.83 | 41.64 | 61.88 | 72.07 | 5 h 14 min |
| standard deviation | 0.06 | 0.09 | 0.37 | 0.49 | 0.64 | 0.65 | |

The formula containing 10 polymer whose Milnacipran concentration per uncoated minigranule is 510 μg and whose film thickness is 54 μm (surface mass equal to 2.32 mg/cm$^2$) does not make it possible to achieve the abovementioned objective in vitro.

On the other hand, surprisingly, the formulas containing 5 and 7.5% polymer, having a Milnacipran concentration per uncoated minigranule of 510 μg, whose film thicknesses are equal to 27 and 40 μm (surface masses equal to 1.16 and 1.74 mg/cm$^2$) achieve the abovementioned objective in vitro.

These formulas containing unit doses of 60 to 240 mg, and more particularly of 60 mg and 120 mg of Milnacipran, can be placed in gelatin capsule of sizes No. 3 or No. 1.

EXAMPLE NO. 12

This example differs from Example 11 in that the nonpareils used in the operation for fixing F2207 in a fluidized air bed have a size of between 500 and 600 microns and not between 710 and 850 microns and in that the plasticizer is dibutyl sebacate and not triethyl citrate.

Depending on the quantity of coating liquid deposited on the microgranules, the amount of dry coating polymer may represent 5, 7.5 or 10% of the weight of uncoated microgranules.

The formula containing 5% polymer whose Milnacipran concentration per minigranule is 175 μg and whose film thickness is equal to 12 μm (surface mass equal to 0.77 mg/cm$^2$) does not make it possible to achieve the abovementioned objective in vitro.

On the other hand, surprisingly, the formulas containing 7.5 and 10% polymer, having a Milnacipran concentration per minigranule of 175 μg, whose film thicknesses are equal to 18 and 28 μm (surface masses equal to 1.15 and 1.54 mg/cm$^2$) achieve the abovementioned objective in vitro.

These formulas containing unit dose of 60 to 240 mg, and more particularly of 120 mg of Milnacipran, can be placed in gelatin capsule of sizes No. 1 or No. 0+.

EXAMPLE NO. 13

This example differs from the preceding examples in that the fixing of Milnacipran is performed according to Example No. 1 and no longer according to Example No. 2. On the other hand, the composition of the coating is identical to that described in Example No. 11.

The operating conditions are modified at the level of the mean air inlet temperature which is set at 50° C.

Depending on the quantity of coating liquid deposited on the microgranules, the amount of dry coating polymer may represent 5, 7.5 and 10% of the weight of the uncoated microgranules.

| | Description of the formulas: | | | | | |
|---|---|---|---|---|---|---|
| | FEW52 | | | | | |
| | 5% | | 7.50% | | 10% | |
| Components | Quantities used (g) | Percentage formula (%) | Quantities used (g) | Percentage formula (%) | Quantities used (g) | Percentage formula (%) |
| Microgranules ex 2 | 500.00 | 92.20 | 500.00 | 88.70 | 500.00 | 85.50 |
| Ethyl cellulose N22NF | 25.00 | 4.60 | 37.50 | 6.75 | 50.00 | 8.50 |
| Dibutyl sebacate | 5.00 | 0.90 | 7.50 | 1.30 | 10.00 | 1.70 |
| Talc | 12.50 | 2.30 | 18.75 | 3.30 | 25.00 | 4.30 |

| | The percentages dissolved are the following: | | | | | |
|---|---|---|---|---|---|---|
| | 0.50 h | 1 h | 2 h | 4 h | 8 h | 12 h | T 50% |
| 5% | 33.41 | 57.10 | 77.95 | 92.75 | 100.36 | 102.15 | 49 min |
| standard deviation | 0.06 | 0.17 | 0.02 | 0.26 | 0.55 | 0.62 | |
| 7.5% | 8.10 | 23.70 | 48.04 | 69.15 | 85.85 | 92.91 | 2 h 08 min |
| standard deviation | 0.25 | 0.47 | 0.36 | 0.19 | 0.60 | 0.68 | |
| 10% | 2.53 | 8.32 | 31.94 | 55.17 | 75.31 | 84.84 | 3 h 18 min |
| standard deviation | 2.71 | 2.26 | 2.49 | 1.55 | 2.15 | 2.65 | |

| | Description of the formulas: | | | | | |
|---|---|---|---|---|---|---|
| | FEW73 | | | | | |
| | 5% | | 7.5% | | 10% | |
| Components | Quantities used (g) | Percentage formula (%) | Quantities used (g) | Percentage formula (%) | Quantities used (g) | Percentage formula (%) |
| Microgranules ex 1 | 1000.00 | 95.15 | 1000.00 | 93.60 | 1000.00 | 92.12 |
| Ethyl cellulose N22NF | 30.00 | 2.85 | 40.00 | 3.75 | 50.00 | 4.60 |
| Triethyl citrate | 15.00 | 1.40 | 20.00 | 1.90 | 25.00 | 2.30 |
| Talc | 16.00 | 0.60 | 8.00 | 0.75 | 10.00 | 0.90 |

| | The percentages dissolved are the following: | | | | | | |
|---|---|---|---|---|---|---|---|
| | 0.50 h | 1 h | 2 h | 4 h | 8 h | 12 h | T 50% |
| 5% | 4.40 | 25.00 | 52.00 | 73.30 | 88.80 | 94.30 | 1 h 54 min |
| standard deviation | 0.70 | 1.40 | 0.80 | 0.50 | 0.40 | 0.50 | |
| 7.5% | 1.10 | 7.70 | 32.70 | 57.90 | 79.30 | 89.20 | 3 h 11 min |
| standard deviation | 0.20 | 0.35 | 0.50 | 0.70 | 0.90 | 0.90 | |
| 10% | 0.50 | 2.40 | 18.70 | 47.30 | 71.60 | 83.90 | 4 h 20 min |
| standard deviation | 0.30 | 0.30 | 0.70 | 1.30 | 1.10 | 0.90 | |

Surprisingly, the formula FEW73 containing 5, 7.5 and 10% ethyl cellulose, having a Milnacipran concentration per minigranule of 510 µg, whose film thicknesses are equal to 28, 43 and 57 µm (surface masses equal to 1.19, 1.79 and 2.38 mg/cm$^2$) achieve the abovementioned objective in vitro. The mean kinetic curves for dissolution in phosphate buffer at pH 7.2 are indicated below in the accompanying Figure No. 1.

These formulas containing the unit doses of 60 to 240 mg, and more particularly of 60 mg and 240 mg of Milnacipran, may be placed gelatin capsule of sizes No. 3 or No. 00.

The proportions of the various components are multiplied by the factor of 15.

The mean air inlet temperature is set at 52° C., the mean spraying rate is 110 g/min, the mean air flow rate is 300 m$^3$/h, the spraying pressure is 3 bar and the diameter of the nozzle 1.2 mm.

Depending on the quantity of coating liquid deposited on the minigranules, the amount of dry coating polymer may represent 5, 7.5 and 10% of the weight of uncoated minigranules.

| | Description of the formulas: | | | | | |
|---|---|---|---|---|---|---|
| | 9584/5 | | 9584/7.5 | | 9584/10 | |
| Components | Quantities used (g) | Percentage formula (%) | Quantities used (g) | Percentage formula (%) | Quantities used (g) | Percentage formula (%) |
| Microgranules ex 1 | 15.00 | 92.20 | 15.00 | 88.70 | 15.00 | 85.50 |
| Ethyl cellulose N22NF | 0.750 | 4.60 | 1.1250 | 6.65 | 1.50 | 8.60 |
| Triethyl citrate | 0.150 | 0.90 | 0.2250 | 1.35 | 0.30 | 1.70 |
| Talc | 0.375 | 2.30 | 0.5625 | 3.30 | 0.75 | 4.30 |

| | The percentages dissolved are the following: | | | | | | |
|---|---|---|---|---|---|---|---|
| | 0.50 h | 1 h | 2 h | 4 h | 8 h | 12 h | T 50% |
| 5% | 6.00 | 25.20 | 49.00 | 70.30 | 87.90 | 95.40 | 2 h 06 min |
| standard deviation | 0.80 | 0.80 | 1.20 | 0.90 | 1.40 | 0.85 | |
| 7.5% | 2.80 | 6.00 | 27.60 | 53.50 | 76.80 | 87.10 | 3 h 45 min |
| standard deviation | 0.80 | 1.20 | 2.10 | 1.80 | 1.70 | 2.30 | |
| 10% | 2.30 | 2.60 | 12.50 | 42.70 | 73.60 | 86.70 | 4 h 50 min |
| standard deviation | 0.60 | 0.95 | 1.30 | 3.65 | 1.60 | 2.00 | |

EXAMPLE NO. 14

This example differs from the preceding one in that the operation for coating the minigranules is performed on a GLATT GPCG5 type pilot apparatus.

Figure 2:
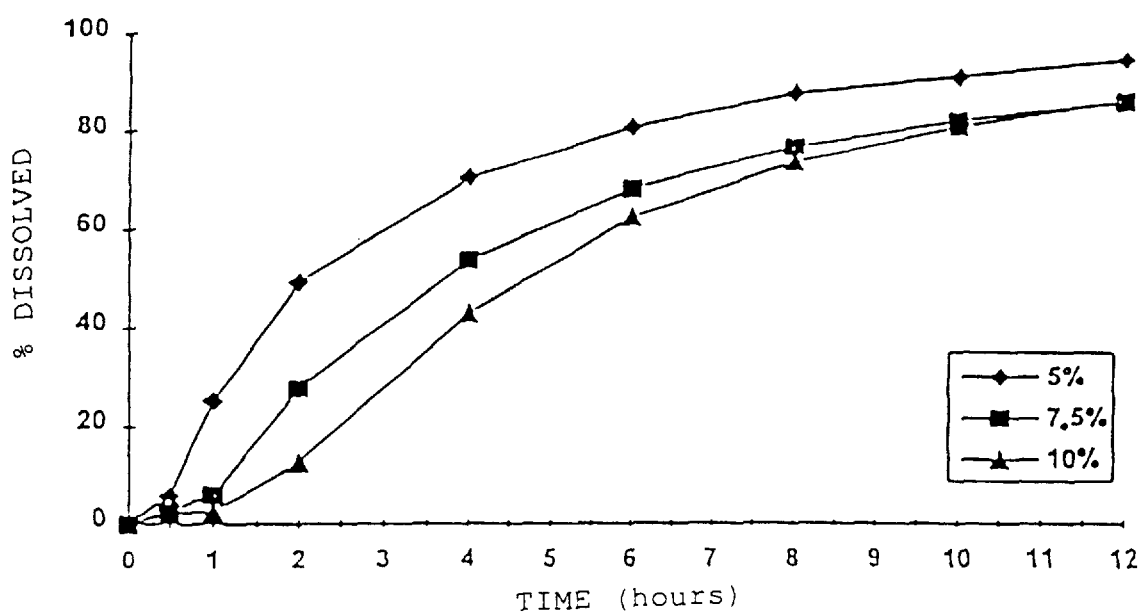

Surprisingly, the formula 9584 containing 5, 7.5 and 10% of ethyl cellulose, having a Milnacipran concentration per uncoated minigranule of 510 µg, whose film thicknesses are equal to 28, 43 and 57 µm (surface masses equal to 1.19, 1.79 and 2.38 mg/cm$^2$) achieve the abovementioned objective in vitro. The mean dissolution curves in vitro in the phosphate buffer at pH 7.2 are given in the accompanying FIG. 2.

These formulas, containing the unit doses of 60 to 240 mg and more particularly of 100 mg and 180 mg of Milnacipran, may be placed in gelatin capsule of sizes No. 1 or No. 0+.

Furthermore, these formulas, packaged in blister pack PVC (250 µm)/PVDC (40 g/m$^2$), aluminium (20 µm) are stable for at least 6 months at 30° C./70% RH.

EXAMPLE NO. 15

This example differs from the preceding one in that the operation for coating the minigranules is carried out in a GLATT GPCG120-type semi-industrial apparatus.

The proportions of the various components are multiplied by a factor of 3.6 compared with Example No. 14 and by a factor of 54 compared with Example 13.

The various operating parameters are consequently adjusted.

Depending on the quality of coating liquid deposited on the minigranules, the amount of dry coating polymer may represent 7.5 and 10% of the weight of uncoated minigranules.

Figure 3:
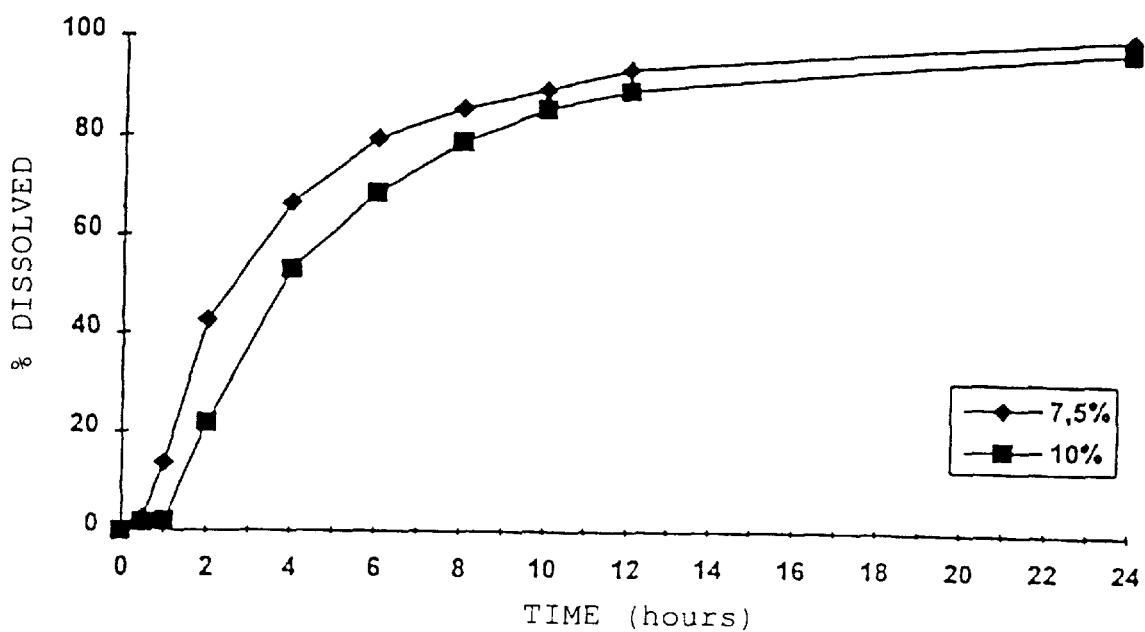

510 µg achieve the abovementioned objective in vitro. The corresponding mean kinetic curves for dissolution are given in the accompanying FIG. 3.

These formulas, containing unit doses of 60 to 240 mg, and more particularly of 60, 120 and 240 mg of Milnacipran, may be placed in gelatin capsule of sizes No. 3, No. 1 or No. 00.

EXAMPLE NO. 16

Example No. 16 differs from all the preceding examples in that the active microgranules are produced according to Example No. 3, that is to say by axial extrusion followed by spheronization. The preparation of the coating solution as

| | Description of the formulas: | | | |
|---|---|---|---|---|
| | 9658/E1 | | 9673/E1 | |
| Components | Quantities used (kg) | Percentage formula (%) | Quantities used (kg) | Percentage formula (%) |
| Minigranules ex 1 | 53.5 | 88.7 | 53.8 | 85.47 |
| Ethyl cellulose ex 1 | 4.013 | 6.65 | 5.38 | 8.54 |
| Triethyl citrate | 0.803 | 1.33 | 1.076 | 1.71 |
| Talc | 2.006 | 3.32 | 2.69 | 4.27 |

| | The percentages dissolved are the following: | | | | | | |
|---|---|---|---|---|---|---|---|
| | 0.50 h | 1 h | 2 h | 4 h | 8 h | 12 h | 24 h |
| 7.50% | 2.6 | 13.9 | 42.6 | 66.2 | 85.6 | 93.4 | 100.6 |
| standard deviation | 0.24 | 1.58 | 1.84 | 1.21 | 0.93 | 0.67 | 1.98 |
| 10% | 1.7 | 2.1 | 21.7 | 52.8 | 78.8 | 89.2 | 97.9 |
| standard deviation | 0.41 | 0.62 | 1.84 | 2.46 | 1.66 | 2.16 | 1.98 |

Surprisingly, the batches 9658/E1 and 9673/E1 containing a Milnacipran concentration per uncoated minigranule of well as the coating operation are performed according to the preceding example.

| | Description of the formulas: | | | |
|---|---|---|---|---|
| | FEW61 | | | |
| | 7.50% | | 10% | |
| Components | Quantities used (g) | Percentage formula (%) | Quantities used (g) | Percentage formula (%) |
| Microgranules ex 3 | 500.00 | 88.70 | 500.00 | 85.50 |
| Ethyl cellulose N22NF | 37.50 | 6.65 | 50.00 | 8.50 |

| | -continued | | | |
|---|---|---|---|---|
| Triethyl citrate | 7.50 | 1.35 | 10.00 | 1.70 |
| Microtalc | 18.75 | 3.30 | 25.00 | 4.30 |

| | The percentages dissolved are the following: | | | | | |
|---|---|---|---|---|---|---|
| | 0.50 h | 1 h | 2 h | 4 h | 8 h | 12 h | T 50% |
| 7.50% | 10.16 | 29.44 | 54.10 | 74.50 | 89.10 | 98.20 | 1 h 46 min |
| standard deviation | 0.37 | 0.93 | 0.93 | 0.84 | 0.56 | 0.39 | |
| 10% | 3.00 | 10.20 | 29.96 | 51.41 | 70.62 | 81.21 | 3 h 40 min |
| standard deviation | 0.14 | 0.44 | 0.47 | 0.70 | 0.72 | 0.66 | |

Surprisingly, the formula FEW61 containing 7.5% and 10% of polymer, having a Milnacipran concentration per minigranule of 500 µg, whose film thicknesses are equal to 21 and 28 µm (surface masses equal to 1.25 and 1.67 mg/cm$^2$) achieve the abovementioned objective in vitro.

These formulas, containing unit doses of 60 to 240 mg, and more particularly 60 mg and 180 mg of Milnacipran, may be placed in gelatin capsule of sizes No. 3 and No. 0+.

EXAMPLE NO. 17

This example differs from the preceding examples in that the active microgranules were produced according to Example No. 5, that is to say by rotogranulation in a fluidized air bed.

The preparation of the coating dispersion as well as the coating operation is performed according to Example No. 10, knowing that in this case Surelease E-7-7060 whose plasticizer is Miglyol and not Dibutyl sebacate is involved.

Depending on the quantity of coating liquid deposited on the minigranules, the amount of dry coating polymer may represent 15 and 20% of the weight of the uncoated minigranules.

| | Description of the formulas: | | | |
|---|---|---|---|---|
| | FEW45 | | | |
| | 15% | | 20% | |
| Components | Quantities used (g) | Percentage formula (%) | Quantities used (g) | Percentage formula (%) |
| Microgranules ex 5 | 500.00 | 86.95 | 500.00 | 83.30 |
| Surelease E-7-7060 | 75.00 | 13.05 | 100.00 | 16.70 |

| | The percentages dissolved are the following: | | | | | |
|---|---|---|---|---|---|---|
| | 0.50 h | 1 h | 2 h | 4 h | 8 h | 12 h | T 50% |
| 15% | 52.60 | 72.30 | 86.00 | 93.60 | 96.10 | 96.50 | 28 min |
| standard deviation | 0.80 | 1.00 | 0.60 | 0.40 | 0.70 | 0.70 | |
| 20% | 29.40 | 45.70 | 62.60 | 78.40 | 90.20 | 94.80 | 1 h 19 min |
| standard deviation | 0.70 | 0.80 | 1.00 | 0.80 | 0.30 | 0.30 | |

The formulas containing 15% and containing 20% of polymer, whose Milnacipran concentration per minigranule is 500 µg and whose film thicknesses are equal to 65 µm and 87.5 µm (surface mass equal to 3.13 and 4.2 mg/cm$^2$), do not make it possible to achieve the abovementioned objective in vitro.

What is claimed is:

1. A prolonged-release pharmaceutical composition provided in a form combining a plurality of minigranules, each of the minigranules containing an active minisphere of Milnacipran, the active minisphere being coated with a film based on at least one polymer insoluble in water but permeable to physiological fluids, having a thickness of between 20 and 100 µm, intended for oral administration in a multiparticulate unit dosage form, the pharmaceutical composition allowing an in vitro dissolution profile of the administered dose measured by the USP XXIII monograph, DISSOLUTION, with the paddle apparatus type 2, the speed of the paddles set at 120 RPM, the dissolution medium is either phosphate buffer (0.066M) pH=7.2, or purified water, wherein the in vitro dissolution profile is:

between 10 and 55% of the dose released in 2 hours, between 40 and 75% of the dose released in 4 hours, between 70 and 90% of the dose released in 8 hours, between 80 and 100% of the dose released in 12 hours.

2. A pharmaceutical composition according to claim 1, wherein each of the minigranules contains an active minisphere comprising from 150 to 1000 µg of Milnacipran.

3. A pharmaceutical composition according to claim 2, wherein the uncoated active minispheres comprise Milnacipran mounted on nonpareils having a particle size of between 200 and 2000 µm with the aid of a binding agent.

4. A pharmaceutical composition according to claim 3, wherein the nonpareils are composed of a mixture of about 75% sucrose and about 25% starch.

5. A pharmaceutical composition according to claim 3, wherein the uncoated active minispheres are manufactured in a pan from nonpareils having a particle size of between 500 and 1000 μm.

6. A pharmaceutical composition according to claim 5, wherein the binding agent used is PVP having a molecular weight of close to 50,000 Da in solution in ethanol, $CH_2Cl_2$, acetone, isopropanol, or mixtures thereof, the mass of PVP representing 3 to 50% of that of the wetting solution and 2 to 4% of that of the uncoated active minispheres.

7. A pharmaceutical composition according to claim 5, wherein the binding agent used is chosen from hydroxypropylmethylcellulose, methyl cellulose or hydroxypropylcellulose, carboxymethylcellulose, gelatin, gum arabic, gum tragacanth, guar gum, pectins, alginates, a solution of sucrose, and mixtures thereof.

8. A pharmaceutical composition according to claim 6, wherein the active minispheres contain, in addition, an antiadhering agent in an amount of 0.5 to 20% by weight relative to the weight of the uncoated active minispheres.

9. A pharmaceutical composition according to claim 7, wherein the active minispheres contain, in addition, an antiadhering agent in an amount of 0.5 to 20% by weight relative to the weight of the uncoated active microspheres.

10. A pharmaceutical composition according to claim 3, wherein the uncoated active minispheres are manufactured in a fluidized air bed by "bottom spray" from nonpareils having a particle size of between 500 and 1000 μm.

11. A pharmaceutical composition according to claim 3, wherein the Milnacipran in dispersion in isopropanol In an amount by mass of 10 to 40%, is sprayed on the nonpareils in an amount by mass of 40 to 50% of the uncoated active minisphere.

12. A pharmaceutical composition according to claim 11, wherein, by using nonpareils having a size of between 710 and 550 μg, uncoated active minispheres containing 440 to 555 μg of Milnacipran are obtained.

13. A pharmaceutical composition according to claim 11, wherein, by using nonpareils having a size of between 850 and 100 μm uncoated active minispheres containing 680 to 850 μg of Milnacipran are obtained.

14. A pharmaceutical composition according to claim 11, wherein, by using nonpareils having a size of between 500 and 600 μm, uncoated active minispheres containing 150 to 185 μg of Milnacipran are obtained.

15. A pharmaceutical composition according to claim 2, wherein the film for coating the active minispheres is obtained with the aid of a coating agent consisting of one or more methacrylic copolymers selected from the group consisting of poly (ethylacrylate, methyl methacrylate) in an aqueous dispersion or selected from the group consisting of poly ethyl acrylate, poly methyl methacrylate, poly trimethylammoniumethyl methacrylate chloride, in an organic solvent or in an aqueous dispersion, the mass of dry polymer used being between 5 and 50% of that of the active minispheres.

16. A pharmaceutical composition according to claim 15, wherein the coating agent contains a filling agent chosen from talc, metal oxides, and silicas.

17. A pharmaceutical composition according to claim 15, wherein the coating agent contains a plasticizer chosen from dimethyl phthalate, triethyl citrate, dibutyl sebacate, dibutyl phthalate, diethyl phthalate, acetyl triethyl citrate, tributyl citrate, acetyl tributyl citrate, triacetin, polyethylene glycols, propylene glycol, glycerois, glycerides, fractionated coconut oil and castor oil.

18. A pharmaceutical composition according to claim 2, wherein the film for coating the active minispheres is obtained with the aid of a coating agent consisting of alkyl cellulose.

19. A pharmaceutical composition according to claim 18, wherein the film for coating the active minispheres is obtained with the aid of a coating agent consisting of ethyl cellulose in solution in a solvent or a mixture of organic solvents, whose dry extract represents 2.5 to 50% of the weight of the active minispheres.

20. A pharmaceutical composition according to claim 18, wherein the film for coating the active minispheres is obtained with the aid of a coating agent consisting of ethyl cellulose in aqueous solution whose dry extract represents 5 to 30% of the weight of the active minispheres.

21. A pharmaceutical composition according to claim 18, wherein the coating agent contains an filling agent chosen from talc, metal oxides, and silicas.

22. A pharmaceutical composition according to claim 18, wherein the coating agent contains a plasticizer chosen from dimethyl phthalate, triethyl citrate, dibutyl sebacate, dibutyl phthalate, diethyl phthalate, acetyl triethyl citrate, tributyl citrate, acetyl tributyl citrate, triacetin, polyethylene glycols, propylene glycol, glycerols, glycerides, fractionated coconut oil and castor oil.

23. A pharmaceutical composition according to claim 19 for which the coating operation carried out in a fluidized air bed involves a coating agent of the ethyl cellulose, or a derivative thereof, in an ethanolic solution at a dry polymer level relative to the weight of the active minispheres of between 3 and 15%, leading to a film thickness of between 20 and 80 μm.

24. A pharmaceutical composition according to claim 22, wherein the coating agent based on ethyl cellulose comprises as plasticizer triethyl citrate or dibutyl sebacate in an amount expressed relative to the dry polymer weight of between 15 and 25%.

25. A pharmaceutical composition according to claim 21, wherein the coating agent based on ethyl cellulose comprises a filling agent whose amount expressed relative to the dry polymer weight is between 20 and 70%.

26. A pharmaceutical composition according to claim 25, wherein the filling agent is talc whose amount expressed relative to the dry polymer weight is 50%.

27. A pharmaceutical composition according to claim 20, for which the film-coating operation carried out in a fluidized air bed involves a coating agent of ethyl cellulose, or a derivative thereof, in an aqueous suspension, at a dry polymer level relative to the weight of the active minispheres of between 12.5% and 17.5%, leading to a film thickness of between 60 and 90 μm.

28. A pharmaceutical composition according to claim 21, wherein the coating film comprises as filling agent talc, at a level expressed relative to the dry weight of the polymer coating agent of between 20 and 70%.

29. A pharmaceutical composition according to claim 15, for which the film coating operation carried out in a fluidized air bed involves a coating agent of poly(ethyl acrylate, methyl methacrylate), or a derivative thereof, in an aqueous dispersion, at a dry polymer level relative to the weight of the active minispheres of between 12.5% and 15% leading to a film thickness of between 60 and 80 μm.

30. A pharmaceutical composition according to claim 16, wherein the coating film comprises as filling agent talc, at a level expressed relative to the dry weight of the polymer coating agent of between 50 and 100%.

31. A pharmaceutical composition according to claim 2, wherein the uncoated active minispheres are obtained by extrusion-spheronization from a mixture comprising Milnacipran, a diluent and a binding agent.

32. A pharmaceutical composition according to claim 31, wherein, the diluent is chosen from microcrystalline cellulose, sodium cellulose, hydroxypropylmethylcellulose, lactose, starch, a mono- or di- or triglyceride, and the binding agent is chosen from hydroxypropylmethylcellulose, methyl cellulose, hydroxypropylcellulose, carboxymethylcellulose, gelatin, a guar gum, gum arabic, gum tragacanth, pectins, alginates, and polyvinylpyrrolidone, and mixtures thereof.

33. A pharmaceutical composition according to claim 32, wherein the diluent used is microcrystalline cellulose in a proportion b mass of between 25 and 75% of the uncoated active minispheres.

34. A pharmaceutical composition according to claim 31, wherein, during the extrusion-spheronization operation, a wetting solvent is used which is chosen from purified water, ethanol, isopropanol and mixtures thereof.

35. A pharmaceutical composition according to claim 1, wherein the administrable Milnacipran unit dose is from 60 to 240 mg.

36. A pharmaceutical composition according to claim 35, wherein the administrable Milnacipran unit dose is about 120 mg.

37. A pharmaceutical composition according to claim 1, wherein the Milnacipran is in the form of a therapeutically equivalent dose of its Cis-D enantiomer.

* * * * *

UNITED STATES PATENT AND TRADEMARK OFFICE
CERTIFICATE OF CORRECTION

PATENT NO. : 6,699,506 B1  Page 1 of 1
DATED : March 2, 2004
INVENTOR(S) : Bruno Paillard et al.

It is certified that error appears in the above-identified patent and that said Letters Patent is hereby corrected as shown below:

Title page,
Item [75], Inventors, "Lauragus" should be -- Lauragais --.

Column 27,
Line 34, "550" should be -- 850 --.
Line 62, "glycerois" should be -- glycerols --.

Column 29,
Line 10, "b" should be -- by --.

Signed and Sealed this

Twenty-fifth Day of May, 2004

JON W. DUDAS
*Acting Director of the United States Patent and Trademark Office*